United States Patent [19]

Robertson et al.

[11] 4,042,602

[45] Aug. 16, 1977

[54] SYNTHESIS OF DIDEOXYZEARALANE AND RELATED COMPOUNDS

[75] Inventors: Donald Edwin Robertson, Terre Haute, Ind.; Wilbert Herbert Urry, Chicago, Ill.; Frank Kavka, St. Louis, Mo.

[73] Assignee: IMC Chemical Group, Inc., Terre Haute, Ind.

[21] Appl. No.: 738,930

[22] Filed: Nov. 4, 1976

[51] Int. Cl.² ............................................ C07D 313/00

[52] U.S. Cl. ................................................ 260/343.41

[58] Field of Search .................................. 260/343.2 F

[56] References Cited

U.S. PATENT DOCUMENTS

| | | | |
|---|---|---|---|
| 3,887,583 | 6/1975 | Wehrmeister et al. ....... | 260/343.2 F |

*Primary Examiner*—James O. Thomas, Jr.
*Assistant Examiner*—Jane T. Fan
*Attorney, Agent, or Firm*—E. A. Figg; Howard E. Post

[57] ABSTRACT

A method is disclosed for preparing dideoxyzearalane and related compounds which comprises reacting a hexahydrozearalin with an organic sulfonyl chloride to form a sulfonate ester derivative; recovering the sulfonate ester derivative; and catalytically dehydrosulfonyloxylating and aromatizing the sulfonate ester derivative to form the desired product.

5 Claims, No Drawings

SYNTHESIS OF DIDEOXYZEARALANE AND RELATED COMPOUNDS

This invention relates to the synthesis of dideoxyzearalane and related compounds (hereinafter sometimes referred to as dideoxyzearalane type compounds). More particularly, the invention relates to a method for preparing a dideoxyzearalane type compound of the formula

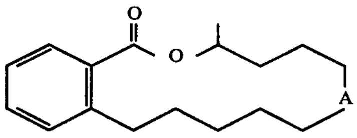

which comprises reacting a hexahydrozearalin of the formula

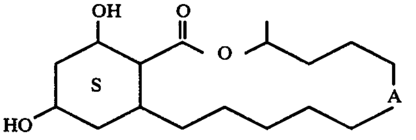

with an organic sulfonyl chloride of the formula $R SO_2 Cl$ under esterifying conditions to form a sulfonate ester derivative of the formula

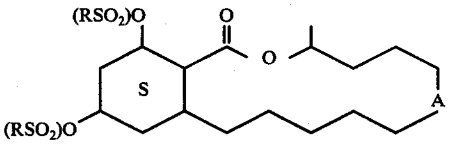
;

recovering the sulfonate ester derivative; and catalytically dehydrosulfonyloxylating and aromatizing the sulfonate ester derivative by heating it to a temperature of from about 125° C to about 250° C in the presence of an organic base and a suitable catalyst under a substantially inert atmosphere to form the dideoxyzearalane type compound; wherein A may be —$CH_2$—, or >$CHOR_1$; $R_1$ may be lower alkyl of from 1 to about 6 carbon atoms, such as methyl, ethyl, propyl, butyl, pentyl, hexyl, etc.; lower alicyclic of from about 1 to about 8 carbon atoms, such as cyclobutyl, cyclohexyl, cyclooctyl, etc.; lower alkanoyl of from 1 to about 6 carbon atoms, such as formyl, acetyl, butyryl, etc.; monocyclic aryl of about 6 to 8 carbon atoms, such as phenyl, tolyl, etc.; monocyclic aralkyl, that is, an alkyl group with an aryl substituent thereon, wherein the alkyl group has 1 to about 5 carbon atoms and the aryl group has about 6 to 8 carbon atoms, such as benzyl, tolylmethyl, etc.; and R is selected from the group consisting of lower alkyl of from 1 to about 10 carbon atoms, such as methyl, ethyl, butyl, 2-ethylhexyl, decyl, etc., and aryl, such as phenyl, p-tolyl, and p-bromophenyl.

Heretofore, the primary method of preparing dideoxyzearalane type compounds has been by selectively etherifying an appropriate hydroxy compound with a heterocyclic compound, such as 2-chlorotetrazole, 2-chlorobenzoxazole, or 1-phenyl-5-chlorotetrazole; then cleaving the heterocyclic ether radicals by catalytic hydrogenolysis to provide the desired dideoxyzearalane type compound. The above method and the utility of dideoxyzearalane type compounds as anabolic and estrogenic agents in animals are disclosed in U.S. Pat. No. 3,887,583, Wehrmeister, H. L., et al., June 3, 1975.

The method of the present invention is advantageous over prior art methods, because, inter alia, the reactant, the organic sulfonyl chloride, is generally more readily available and is currently less costly than the heterocyclic compounds of the prior art method.

The hexahydrozearalins used as starting materials for the method of the present invention may be prepared by saturating the aromatic ring of zearalenone or derivatives thereof, by known methods. Zearalenone, which is represented by the following structural formula, is a natural metabolite of the organism, *Giberella zeae,* and may be prepared by cultivation of a zearalenone-producing strain of that microorganism on a suitable nutrient medium:

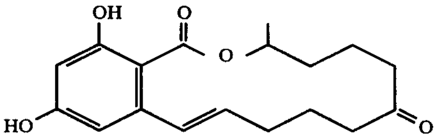

The production of zearalenone is taught, for instance, by Andrews, F. N., et al., U.S. Pat. No. 3,196,019, July 20, 1965.

Hexahydrozearalins are produced from zearalenone or zearalenone derivatives by catalytic hydrogenation as taught for example, in U.S. Pat. No. 3,373,037, Abbott, R. L., Mar. 12, 1968, incorporated herein by reference.

In formulae herein

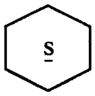

indicates a saturated, i.e. cyclohexyl, ring. The nomenclature used herein generally conforms to that described by Shipchandler, M. T., *Heterocycles* 3, 471(1975).

The organic sulfonyl chloride used as a reactant in the method of this invention may be an alkane sulfonyl chloride, containing from 1 to about 10 carbon atoms, or an aryl sulfonyl chloride such as benzene sulfonyl chloride, p-toluene sulfonyl chloride, or p-bromobenzene sulfonyl chloride. Preferred organic sulfonyl chlorides are alkane sulfonyl chlorides containing from 1 to about 5 carbon atoms, the most preferred being methane sulfonyl chloride.

The reaction of the organic sulfonyl chloride with hexahydrozearalin is conducted under esterifying conditions. Such esterifying conditions advantageously include conducting the reaction in a non-reactive solvent, i.e. a solvent which does not react with the reactants or products or otherwise deleteriously affect the reaction. Such solvents generally include aromatic or lower aliphatic organic solvents which do not contain active hydrogens, e.g. normally liquid aliphatic hydrocarbons, of from about 6 to about 10 carbon atoms, such as cyclohexane, octane, decane, etc.; aliphatic ethers of from about 4 to about 10 carbon atoms, such as tetrahydrofuran, dipropyl ether, dibutyl ether, etc.; aromatic hydrocarbons of from about 6 to 10 carbon atoms, such as benzene, toluene, xylene, pyridine, etc.; tertiary aliphatic amines of from 6 to about 10 carbon atoms, such as triethylamine, tripropylamine, etc.; and aliphatic ketones of from about 3 to about 8 carbon atoms, such as acetone, methyl ethyl ketone, dibutyl ketone, etc.

The reaction medium also advantageously includes a base in an amount sufficient to neutralize liberated hydrogen chloride and catalyze the reaction i.e., an amount at least equivalent to the organic sulfonyl chloride. The base is advantageously an organic base such as pyridine or a tertiary lower aliphatic amine, e.g. amines having from about 6 to 10 carbon atoms such as triethyl amine, tripropyl amine, etc. The preferred base is pyridine, which can be effectively used as both the solvent and the base.

The reaction temperature is not critical; however, the time required for substantially complete reaction may vary with the temperature. Generally, the reaction temperature is from about 0° C to about 100° C, preferably from about 20° C to about 70° C. The reaction is usually complete within about 24 hours at about room temperature or less at elevated temperatures.

The resulting sulfonate ester derivative is recovered from the reaction mixture by any suitable method, such as crystallization or extraction. The sulfonate ester derivative may precipitate from the reaction mixture, thus allowing its recovery directly, e.g. by filtration. If the sulfonate ester derivative does not precipitate from the reaction mixture, the preferred recovery method is to mix the reaction mixture with cold water, then extract the water mixture with a suitable immiscible solvent such as methylene chloride or chloroform. The extract is then dried e.g. with $Na_2SO_4$ and the solvent removed by evaporation or distillation at reduced pressure. The resulting product may be further purified by recrystallization.

The sulfonate ester derivative is subjected to simultaneous dehydrosulfonyloxylation and aromatization, i.e. removal of four hydrogens and the two sulfonyloxy groups from the six-member ring, by heating it to a temperature of from about 75° C to about 250° C, preferably about 140° C to about 200° C, in the presence of an organic base and a suitable catalyst under a substantially inert atmosphere. The organic base is advantageously an organic nitrogen compound such as tertiary lower aliphatic amine of from about 6 to about 10 carbon atoms, e.g. triethylamine, tripropylamine, etc., or an aromatic nitrogen compound such as pyridine, any isomeric form of lutidine, e.g. 2,3-lutidine, 2,4-lutidine, 2,5-lutidine, 2,6-lutidine, 3,4-lutidine, or 3,5-lutidine, any isomeric form of ethylmethyl-pyridine, e.g. 2-ethyl-3-methylpyridine, 2-ethyl-4-methylpyridine, 2-ethyl-5-methylpyridine, 2-ethyl-6-methylpyridine, 3-ethyl-4-methylpyridine, 3-ethyl-5-methylpyridine, 2-methyl-3-ethylpyridine, 2-methyl-4-ethylpyridine, 2-methyl-5-ethylpyridine, or 3-methyl-4-ethylpyridine, or any isomeric form of diethyl-pyridine, e.g. 2,3-diethylpyridine, 2,4-diethylpyridine, 2,5-diethylpyridine, 2,6-diethylpyridine, 3,4-diethylpyridine, or 3,5-diethylpyridine. The organic base is employed in an amount sufficient to catalyze the reaction, and is preferably present in a molar amount at least equivalent to the sulfonate ester groups. The most preferred method of conducting the reaction is to employ the organic base as the reaction solvent and refluxing the reaction mixture. 5-Ethyl-2-methylpyridine is the preferred base for such application because of its relatively high boiling point.

Any suitable catalyst may be utilized in the reaction in catalytic amounts. The preferred catalyst is palladium, which is advantageously deposited on finely divided carbon in an amount of from about 1% to about 10% by wt. A 5% by wt. palladium on carbon catalyst is preferably employed in an amount of from 0.5 g to 2 g per gram of sulfonate ester derivative.

The reaction may be conducted under any inert atmosphere, such as dry nitrogen, helium, argon, etc. The preferred atmosphere is dry nitorgen. The reaction is conducted until the dehydrosulfonyloxylation and aromatization are substantially complete. A reaction time of from about 1 hour to about 10 hours is generally sufficient.

The dideoxyzearalane type compound may be recovered by any suitable method. A convenient recovery method involves removal of the catalyst and other solids by filtration or centrifugation, acidification of the filtrate with dilute hydrochloric acid, extraction of the filtrate with a suitable immiscible solvent such as chloroform or methylene chloride, and removal of the immiscible solvent by evaporation or distillation. The residue containing the dideoxyzearalane type compound may be further purified, e.g. by recrystallization, if desired.

The invention is further illustrated by the following examples which are not intended to be limiting.

EXAMPLE I

Hexahydrozearalane (1.0 g, 0.0032 mole) was dissolved in 4 ml of dry pyridine and methanesulfonyl chloride (0.8 g, 7 millimoles) was added dropwise with stirring and cooling. The mixture was stirred for 22 hours at room temperature, poured into 60 ml of ice water, and the precipitate was removed by filtration and washed with water. Thin-layer chromatography indicated that the reaction was not complete, therefore, the product was redissolved in 4 ml of dry pyridine, methanesulfonyl chloride (0.9 g, 7.9 millimoles) was added, and the mixture was stirred at 55°-60° C. After 5 hours, thin-layer chromatography indicated that the reaction was still not complete. Additional methanesulfonyl chloride (.15 g, 1.3 millimoles) was added, and the mixture was stirred for an additional 30 min. at 55°-60° C, and stored overnight at room temperature. The mixture was then poured into 100 ml of ice water, and the precipitate was filtered and washed with water to give 1.23 g of light brown product. The product was dissolved in benzene and chromatographed on a silica gel column using the following gradient eluent: benzene, benzene-ethyl acetate (58:2, 55:5, 5:1, 4:2, 2:4), ethyl acetate in 60 ml portions. Fractions were taken and evaluated by thin-layer chromatography. The main fractions were combined and the solvent removed by evaporation, yielding about 1 g of product for which the melting point was 164°-165° C and the nuclear magnetic resonance spectrum was consistent with the structure of di(methanesulfonyl)hexahydrozearalane.

Di(methanesulfonyl)hexahydrozearalane (0.33 g, 0.74 millimole), 5% palladium on char (0.33 g), and 50ml of distilled and dried 5-ethyl-2-methylpyridine were refluxed with stirring for 3 hours under a nitrogen atmosphere. The mixture was filtered, the catalyst was washed with chloroform and the combined filtrate and washings were poured into a mixture of 35 ml of concentrated hydrochloric acid and 310 ml of ice water. The mixture was extracted with chloroform, the chloroform layers were washed with dilute hydrochloric acid, water, and sodium bicarbonate solution, dried over sodium sulfate and concentrated. Thin-layer chromatography indicated that the primary component was dideoxyzearalane and a minor component was di(methanesulfonyl)hexahydrozearalane. The nuclear magnetic resonance spectrum also indicated that mixture. High pressure liquid chromatography showed 7 76% dideoxyzearalane or a 77% yield.

EXAMPLE II

A solution of hexahydrozearalane (2.0 g, 0.0064 mole, mp 168°-169°) and methanesulfonyl chloride (1.2 ml, 1.8 g, 0.016 mole) in anhydrous pyridine (8 ml) was heated at 55°-60° for 5 hours with stirring. Additional methanesulfonyl chloride (0.2 ml) was added and the heating continued for 30 minutes. The solution was allowed to stand overnight at ambient temperatures and was poured into water (220 ml) with vigorous stirring. The precipitate was filtered off and washed with water (100 ml). The cake was dried under a heat lamp yielding 2.58 g (86% of theoretical yield of di(methanesulfonyl)-hexahydrozearalane) of white crystals: mp 145°-150°; TLC (EtOAc, $H_2SO_4$ visualization) Rf's 0.43 weak, 0.54 and 0.70 weak. Recrystallization from benzenehexanes (40°, 109 ml and 250 ml) yielded 1.50 g (50% of theory) of white crystals: mp 159°-161°; TLC (EtOAc, $H_2SO_4$ visualization) Rf's 0.53. Concentration of the filtrate yielded 0.65 g (21.7% of theory) of white crystals: mp 156°-158°; TLC (EtOAc, $H_2SO_4$ visualization) Rf's 0.55.

A solution of di(methanesulfonyl)hexahydrozearalane (0.66 g, 0.0014 mole, mp 159°-161° C) in anhydrous 5-ethyl-2-methylpyridine (100 ml distilled from BaO) containing dispersed palladium (0.66 g, 5% Pd/C) was heated under reflux for 3 hours under a nitrogen atmosphere. The mixture was filtered and the cake was washed with $CHCl_3$ (2×50 ml). The filtrate and wash were poured into 1.2 M HCl (690 ml). The mixture was extracted with $CHCl_3$ (5×100 ml). The extracts were washed with: 2M HCl (240 ml), $H_2O$ (200 ml), 10% aqueous $NaHCO_3$ (200 ml), and $H_2O$ (200 ml). The extracts were dried ($Na_2SO_4$) and concentrated in vacuum yielding 0.47 g (theory 0.386 g dideoxyzearalane) of an amber oil: TLC (ETOAc, $H_2SO_4$ visualization) Rf's 0 moderate, 0.65 weak non-UV sensitive, 0.73 heavy (dideoxyzearalane, Rf's 0.72); high pressure liquid chromatography found 77 weight percent dideoxyzearalane equivalent to 0.362 g in product or a 94% conversion; the nuclear magnetic resonance spectrum was consistent with the structure of dideoxyzearalane.

EXAMPLE III

The experiment of Example I is repeated in all essential details except O[6']-ethylhexahydrozearalanol of the formula

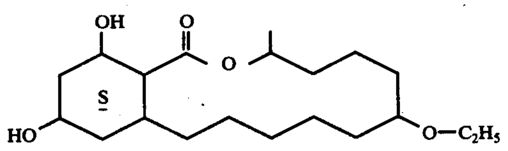

is substituted for hexahydrozearalane and ethanesulfonyl chloride is substituted for methanesulfonyl chloride. The reaction should yield O[6']-ethyldideoxyzearalanol of the formula

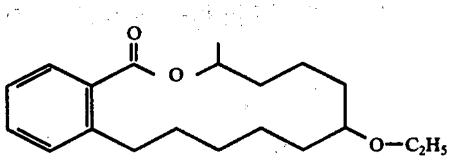

EXAMPLE IV

The experiment of Example I is repeated in all essential details except O[6']-benzylhexahydrozearalanol of the formula

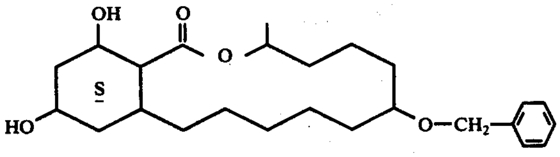

is substituted for hexahydrozearalane and butanesulfonyl chloride is substituted for methanesulfonyl chloride. The reaction should yield O[6']-benzyldideoxyzearalanol of the formula

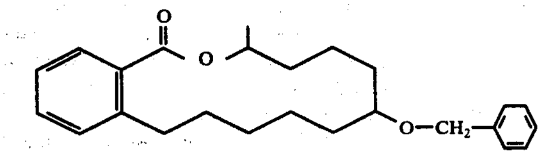

EXAMPLE V

The experiment of Example I is repeated in all essential details except O[6']-acetylhexahydrozearalanol of the formula

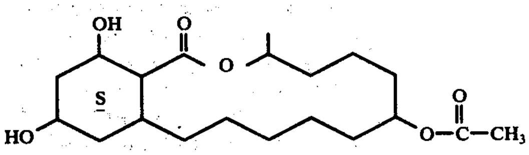

is substituted for hexahydrozearalane, and p-toluenesulfonyl chloride is substituted for methanesulfonyl chloride. The reaction should yield O[6']-acetyldideoxyzearalanol of the formula

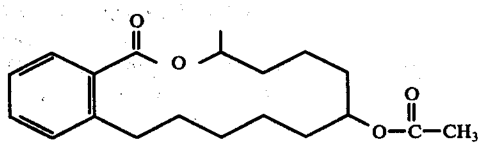

We claim:

1. A method for preparing a dideoxyzearalane type compound of the formula

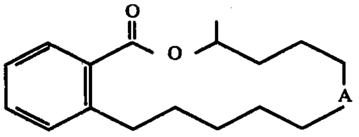

comprising the steps of reacting a hexahydrozearalin of the formula

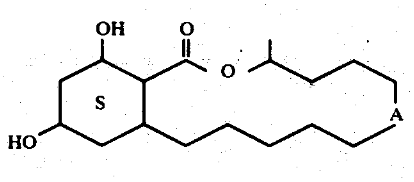

with an organic sulfonyl chloride of the formula $R SO_2 Cl$ under esterifying conditions to form a sulfonate ester derivative of the formula

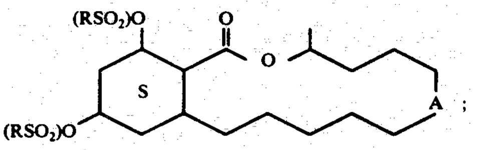

recovering the sulfonate ester derivative; and catalytically dehydrosulfonyloxylating and aromatizing the sulfonate ester derivative by heating it to a temperature of from about 75° C to about 250° C in the presence of an organic base and a palladium catalyst under a substantially inert atmosphere to form the dideoxyzearalane type compound; wherein A is $-CH_2-$, or $>CHOR_1$; $R_1$ is lower alkyl of from 1 to about 6 carbon atoms, lower alicyclic of from about 4 to about 8 carbon atoms; lower alkanoyl of from 1 to about 6 carbon atoms, monocyclic aryl of about 6 to 8 carbon atoms, or monocyclic aralkyl, wherein the alkyl group has from 1 to about 5 carbon atoms and the aryl group has about 6 to 8 carbon atoms; and R is selected from the group consisting of lower alkyl of from 1 to about 10 carbon atoms, phenyl, p-tolyl, and p-bromophenyl.

2. The method of claim 1 wherein the esterifying conditions include a non-reactive, aromatic or lower aliphatic organic reaction solvent containing an organic base selected from the group consisting of pyridine and tertiary lower aliphatic amines of from about 6 to 10 carbon atoms in an amount at least equimolar to the organic sulfonyl chloride; and a reaction temperature of from about 0° C to about 75° C; and the dehydrosulfonyloxylation and aromatization are conducted at a temperature of from about 140° C to about 200° C, the organic base is a member selected from the group consisting of tertiary lower aliphatic amines of from about 6 to about 10 carbon atoms, pyridine, any isomeric form of lutidine, any isomeric form of ethylmethylpyridine, and any isomeric form of diethylpyridine and the organic base is employed in a molar amount at least about equivalent to the sulfonate ester groups; the catalyst is palladium deposited on finely divided carbon and is employed in a catalytic amount; and the inert atmosphere is dry nitrogen.

3. The method of claim 2 wherein the dideoxyzearalane type compound is dideoxyzearalane, the hexahydrozearalin is hexahydrozearalane, and the organic sulfonyl chloride is methanesulfonyl chloride.

4. The method of claim 2 wherein the dideoxyzearalane type compound is $O^{6'}$-acetyldideoxyzearalanol of the formula

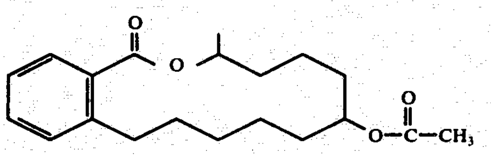

the hexahydrozearalin is $O^{6'}$-acetylhexahydrozearalanol of the formula

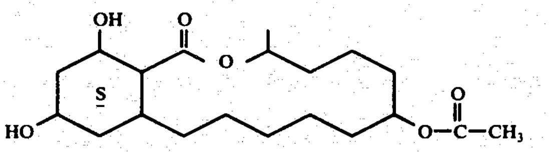

and the organic sulfonyl chloride is ethanesulfonyl chloride.

5. The method of claim 2 wherein the dideoxyzearalane type compound is $O^{6'}$-benzyldideoxyzearalanol of the formula

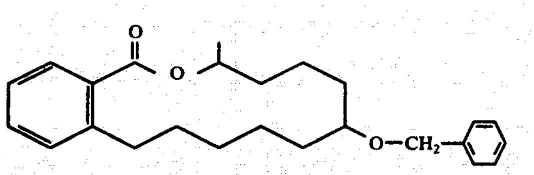

the hexahydrozearalin is $O^{6'}$-benzylhexahydrozearalanol of the formula

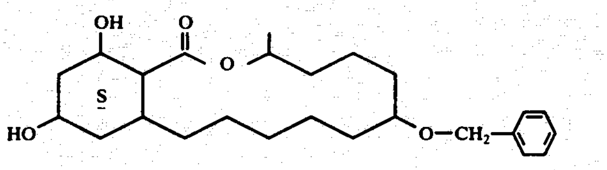

and the organic sulfonyl chloride is p-toluenesulfonyl chloride.

* * * * *